(12) United States Patent
Peterson et al.

(10) Patent No.: US 11,660,425 B2
(45) Date of Patent: May 30, 2023

(54) PERFUSION CATHETERS AND RELATED METHODS

(71) Applicant: Teleflex Life Sciences Limited, Valletta (MT)

(72) Inventors: Dean Peterson, Minneapolis, MN (US); Loic Van Horne, Minneapolis, MN (US); Danny Jester, Eden Prairie, MN (US)

(73) Assignee: Teleflex Life Sciences Limited, Valletta (MT)

( * ) Notice: Subject to any disclaimer, the term of this patent is extended or adjusted under 35 U.S.C. 154(b) by 85 days.

(21) Appl. No.: 17/245,725

(22) Filed: Apr. 30, 2021

(65) Prior Publication Data

US 2021/0260347 A1    Aug. 26, 2021

Related U.S. Application Data

(63) Continuation of application No. 16/414,921, filed on May 17, 2019, now Pat. No. 11,027,102.
(Continued)

(51) Int. Cl.
*A61M 25/10* (2013.01)
*A61B 17/12* (2006.01)
*A61B 17/22* (2006.01)

(52) U.S. Cl.
CPC ..... *A61M 25/1002* (2013.01); *A61B 17/1204* (2013.01); *A61B 17/12109* (2013.01);
(Continued)

(58) Field of Classification Search
CPC ........ A61M 25/1002; A61M 25/10184; A61M 25/104; A61M 2025/1097;
(Continued)

(56) References Cited

U.S. PATENT DOCUMENTS

| 4,762,130 A | 8/1988 | Fogarty et al. |
| 4,790,315 A | 12/1988 | Mueller, Jr. et al. |

(Continued)

FOREIGN PATENT DOCUMENTS

| CN | 108325050 A | 7/2018 |
| EP | 2689789 A1 | 1/2014 |

(Continued)

OTHER PUBLICATIONS

Comments on Statement of Reasons for Allowance filed May 3, 2021, in U.S. Appl. No. 16/414,921.
(Continued)

*Primary Examiner* — Richard G Louis
(74) *Attorney, Agent, or Firm* — Robert B. Madden

(57) ABSTRACT

This patent document discloses perfusion catheters and related methods for treating complications related to CTO interventions or dilating a vessel occlusion while maintaining a passage through the treated vessel segment. A perfusion catheter can include an inflatable balloon coiled in a helical manner around a central axis into a series of windings. An inner surface of the series of windings, when inflated, can define a passage through the inflatable balloon. A catheter can also include an elongate shaft extending from a proximal portion to a distal portion, having an inner surface that defines a lumen for providing inflation fluid to, or withdrawing inflation fluid from, a distal end of the inflatable balloon. A catheter can further include a guidewire support tube including a lumen, separate from the lumen from the elongate shaft and the passage through the inflatable balloon, for receiving a guidewire.

19 Claims, 8 Drawing Sheets

Related U.S. Application Data

(60) Provisional application No. 62/701,362, filed on Jul. 20, 2018.

(52) U.S. Cl.
CPC ..... *A61B 17/12136* (2013.01); *A61M 25/104* (2013.01); *A61M 25/10184* (2013.11); *A61B 2017/22051* (2013.01); *A61M 2025/1097* (2013.01)

(58) Field of Classification Search
CPC ...... A61M 25/1029; A61M 2025/1056; A61B 17/1204; A61B 17/12109; A61B 17/12136; A61B 2017/22051
See application file for complete search history.

(56) References Cited

U.S. PATENT DOCUMENTS

| | | | |
|---|---|---|---|
| 4,909,252 | A | 3/1990 | Goldberger |
| 4,944,745 | A | 7/1990 | Sogard et al. |
| 5,047,045 | A | 9/1991 | Arney et al. |
| 5,087,247 | A | 2/1992 | Horn et al. |
| 5,181,911 | A | 1/1993 | Shturman |
| 5,195,969 | A | 3/1993 | Wang et al. |
| 5,226,888 | A | 7/1993 | Arney |
| 5,226,889 | A | 7/1993 | Sheiban |
| 5,252,159 | A | 10/1993 | Arney |
| 5,257,974 | A | 11/1993 | Cox |
| 5,295,995 | A | 3/1994 | Kleiman |
| 5,368,566 | A | 11/1994 | Crocker |
| 5,370,691 | A | 12/1994 | Samson |
| 5,421,826 | A | 6/1995 | Crocker et al. |
| 5,439,445 | A | 8/1995 | Kontos |
| 5,470,314 | A | 11/1995 | Walinsky |
| 5,505,702 | A | 4/1996 | Arney |
| 5,536,250 | A | 7/1996 | Klein et al. |
| 5,545,135 | A | 8/1996 | Iacob et al. |
| 5,545,138 | A | 8/1996 | Fugoso et al. |
| 5,549,551 | A | 8/1996 | Peacock, III et al. |
| 5,549,552 | A | 8/1996 | Peters et al. |
| 5,554,119 | A | 9/1996 | Harrison et al. |
| 5,556,382 | A | 9/1996 | Adams |
| 5,558,642 | A | 9/1996 | Schweich et al. |
| 5,569,184 | A | 10/1996 | Crocker et al. |
| 5,613,948 | A | 3/1997 | Avellanet |
| 5,643,171 | A | 7/1997 | Bradshaw et al. |
| 5,649,978 | A | 7/1997 | Samson |
| 5,683,451 | A | 11/1997 | Lenker et al. |
| 5,690,642 | A | 11/1997 | Osborne et al. |
| 5,716,340 | A | 2/1998 | Schweich et al. |
| 5,720,723 | A | 2/1998 | Adams |
| 5,738,667 | A | 4/1998 | Solar |
| 5,800,450 | A | 9/1998 | Lary et al. |
| 5,855,546 | A | 1/1999 | Hastings et al. |
| 5,879,369 | A | 3/1999 | Ishida |
| 5,882,290 | A | 3/1999 | Kume |
| 5,891,154 | A | 4/1999 | Loeffler |
| 5,961,490 | A | 10/1999 | Adams |
| 5,985,307 | A | 11/1999 | Hanson et al. |
| 6,083,215 | A | 7/2000 | Milavetz |
| 6,110,097 | A | 8/2000 | Hastings et al. |
| 6,187,014 | B1 | 2/2001 | Goodin et al. |
| 6,190,355 | B1 | 2/2001 | Hastings |
| 6,245,040 | B1 | 6/2001 | Inderbitzen et al. |
| 6,361,529 | B1 | 3/2002 | Goodin et al. |
| 6,503,224 | B1 | 1/2003 | Forman et al. |
| 6,506,180 | B1 | 1/2003 | Lary |
| 6,673,040 | B1 | 1/2004 | Samson et al. |
| 6,945,957 | B2 | 9/2005 | Freyman |
| 7,147,655 | B2 | 12/2006 | Chermoni |
| 7,563,247 | B2 | 7/2009 | Maguire et al. |
| 8,049,061 | B2 | 11/2011 | Ehrenreich et al. |
| 8,430,845 | B2 | 4/2013 | Wahr et al. |
| 8,469,925 | B2 | 6/2013 | Rowe et al. |
| 8,486,014 | B2 | 7/2013 | Kelly et al. |
| 9,968,763 | B2 | 5/2018 | Root et al. |
| 10,159,821 | B2 | 12/2018 | Root et al. |
| 10,864,355 | B2 | 12/2020 | Root et al. |
| 11,027,102 | B2 | 6/2021 | Peterson et al. |
| 11,511,086 | B2 | 11/2022 | Bridgeman et al. |
| 2002/0077591 | A1 | 6/2002 | Happ et al. |
| 2002/0151880 | A1 | 10/2002 | Lafontaine |
| 2003/0032920 | A1 | 2/2003 | Wantink |
| 2003/0040704 | A1 | 2/2003 | Dorros et al. |
| 2003/0120208 | A1 | 6/2003 | Houser et al. |
| 2003/0233068 | A1 | 12/2003 | Jayaraman |
| 2004/0093008 | A1 | 5/2004 | Zamore |
| 2004/0142704 | A1 | 7/2004 | Scholz |
| 2004/0230178 | A1 | 11/2004 | Wu |
| 2005/0075662 | A1 | 4/2005 | Pedersen et al. |
| 2006/0142704 | A1 | 6/2006 | Lentz |
| 2006/0210605 | A1 | 9/2006 | Chang et al. |
| 2006/0259062 | A1 | 11/2006 | Konstantino |
| 2008/0200896 | A1 | 8/2008 | Shmulewitz et al. |
| 2009/0105641 | A1* | 4/2009 | Nissl ............... A61M 25/104 604/101.02 |
| 2011/0009818 | A1 | 1/2011 | Goff |
| 2011/0264039 | A1 | 10/2011 | Thielen et al. |
| 2012/0232640 | A1 | 9/2012 | Horvers |
| 2012/0245520 | A1* | 9/2012 | Kelly ............... A61M 25/1029 604/103.09 |
| 2013/0018448 | A1 | 1/2013 | Folan et al. |
| 2013/0261729 | A1 | 10/2013 | Gillick et al. |
| 2015/0032148 | A1 | 1/2015 | Golan |
| 2015/0250577 | A1 | 9/2015 | Hall |
| 2015/0272732 | A1 | 10/2015 | Tilson et al. |
| 2016/0066932 | A1 | 3/2016 | Root et al. |
| 2017/0143355 | A1 | 5/2017 | Nicholson et al. |
| 2019/0083760 | A1 | 3/2019 | Root et al. |
| 2020/0023169 | A1 | 1/2020 | Peterson et al. |
| 2020/0054865 | A1 | 2/2020 | Bridgeman et al. |
| 2023/0028504 | A1 | 1/2023 | Bridgeman et al. |

FOREIGN PATENT DOCUMENTS

| | | |
|---|---|---|
| EP | 3125781 B1 | 11/2018 |
| EP | 3400886 A1 | 11/2018 |
| JP | H09164191 A | 6/1997 |
| JP | 2002503986 A | 2/2002 |
| JP | 2005230579 A | 9/2005 |
| JP | 2011505918 A | 3/2011 |
| JP | 6097447 B2 | 3/2017 |
| JP | 6326517 B2 | 4/2018 |
| WO | 1993007929 A1 | 4/1993 |
| WO | 1994026206 A1 | 11/1994 |
| WO | 1997032626 A2 | 9/1997 |
| WO | 1998055179 A1 | 12/1998 |
| WO | 2000023139 A1 | 4/2000 |
| WO | 2005027995 A2 | 3/2005 |
| WO | 2012037507 A1 | 3/2012 |
| WO | 2014055547 A1 | 4/2014 |
| WO | 2016040579 A1 | 3/2016 |
| WO | 2017139357 A1 | 8/2017 |

OTHER PUBLICATIONS

Non-Final Office Action dated Dec. 24, 2020, in U.S. Appl. No. 16/414,921.
Notice of Allowance dated Apr. 7, 2021, in U.S. Appl. No. 16/414,921.
Response to Non-Final Office Action filed Mar. 22, 2021, in U.S. Appl. No. 16/414,921.
Non-Final Office Action dated Sep. 29, 2022, in U.S. Appl. No. 17/093,873.
European Search Report and Search Opinion dated Oct. 12, 2018, in European application EP18177601.4.
European Search Report dated Jan. 1, 2020, in EP application No. 19178585.6.
International Search Report dated Nov. 24, 2015, from PCT application PCT/US2015/049356 filed Sep. 10, 2015.
PCT International Search Report dated Dec. 6, 2019, in PCT application No. PCT/US2019/046545.

(56) References Cited

OTHER PUBLICATIONS

PCT partial international search report dated Dec. 6, 2019, in PCT application No. PCT/US2019/046545.
PCT Written Opinion dated Dec. 6, 2019, in PCT application No. PCT/US2019/046545.
Written Opinion dated Nov. 24, 2015, from PCT application PCT/US2015/049356 filed Sep. 10, 2015.
Response to Final Office Action filed Feb. 22, 2023, in U.S. Appl. No. 17/093,873.
Final Office Action dated Jan. 19, 2023, in U.S. Appl. No. 17/093,873.
Response to non-final office action filed Dec. 30, 2022, in U.S. Appl. No. 17/093,873.

* cited by examiner

1500

1582
Passing a perfusion catheter, including a balloon, and an elongate shaft that is attached to the balloon, into a blood vessel until the balloon is positioned adjacent a perforation or dissection in a wall of the blood vessel

1584
Inflating the balloon to seal the perforation or dissection in the wall of the blood vessel including urging fluid through a lumen of the elongate shaft and into the balloon to inflate a series of helical windings of the balloon

1586
The balloon, upon inflation, moving from a deflated configuration to an inflated configuration at which an outer surface of the balloon engages the wall of the blood vessel and an inner surface of the balloon's series of helical windings defines a passage

1588
After inflating the balloon, passing a treatment device at least partially through the passage, including receiving, in a distal-to-proximal direction, or delivering, in a proximal-to-distal direction, the treatment device

1590
Deflating the balloon by withdrawing fluid from the balloon in a distal-to-proximal direction of the balloon

1592
Retracting the perfusion catheter from the blood vessel

*FIG. 15*

PERFUSION CATHETERS AND RELATED METHODS

CLAIM OF PRIORITY

This non-provisional patent document is a continuation of U.S. patent application Ser. No. 16/414,921, entitled "PERFUSION CATHETERS AND RELATED METHODS" and filed May 17, 2019, now U.S. Pat. No. 11,027,102, which claims the benefit of priority under 35 U.S.C. § 119(e) to U.S. Provisional Patent Application Ser. No. 62/701,362, entitled "PERFUSION CATHETERS AND RELATED METHODS" and filed on Jul. 20, 2018, each of which is herein incorporated by reference in its entirety.

TECHNICAL FIELD

The subject matter of this patent document relates to the field of medical devices. More particularly, but not by way of limitation, the subject matter relates to catheters and related methods for sealing a vessel perforation or dissection or dilating a vessel occlusion.

BACKGROUND

A severe or chronic total occlusion (CTO) is a vessel blockage that prevents blood flow beyond the occlusion. Chronic total occlusions most often occur in coronary and peripheral arteries and result from atherosclerosis.

A procedure for treating CTOs is percutaneous transluminal angioplasty.

During an angioplasty procedure, access to a desired blood vessel is obtained and a guidewire is introduced into the blood vessel. The guidewire is maneuvered into place, including being passed into and through the occlusion, and acts as a guide for positioning a subsequent treatment device used to dilate or otherwise treat the vessel occlusion. The treatment device can be advanced over the guidewire so that its distal portion is positioned within the occlusion. A dilatation balloon at the distal portion of the treatment device can then be inflated to apply radial pressure to the occlusive material and adjacent inner wall portions of the vessel, thereby clearing the occlusion to enable better blood flow.

OVERVIEW

The present inventors recognize that CTOs are one of the most challenging lesion subsets in interventional cardiology to treat due to their established occlusive structure. Complications related to CTO interventions include vessel wall perforation and dissection. If not treated without delay, blood hemorrhaging through the perforation or dissection can lead to death of the patient within minutes.

The present inventors also recognize that sealing of the vessel perforation or dissection using conventional balloon catheters causes complete interruption of blood flow within the damaged vessel while the catheter's balloon is inflated. Keeping the balloon inflated for an extended period can risk damage to bodily regions nourished by the vessel-regions already weakened by insufficient blood supply. For example, prolonged dilations of several minutes may need to be employed to effectively treat a perforation. Yet, most adults are only able to withstand non-perfusion dilation of 30-60 seconds without significant side effects.

The present inventors further recognize that after treating a vessel, the catheter balloon may not sufficiently deflate, making it difficult or even impossible to pull the balloon back into the guide catheter and remove it from the patient. The inventors particularly recognize that fluid remaining in the balloon is often pushed distally as the balloon is pulled proximally into the guide catheter, thereby trapping fluid in the balloon and preventing complete deflation, which also increases the likelihood of puncturing the balloon.

The present perfusion catheters can be quickly and easily deployed, inflated, and deflated in a damaged vessel. The catheters can also provide a passage (or flow lumen) formed upon inflation of its balloon. A perfusion catheter can include a balloon formed of an inflatable tube and an elongate shaft having a lumen for providing inflation fluid to, or withdrawing inflation fluid from, the balloon. The inflatable tube can be coiled in a helical manner around a central axis into a series of windings. Adjacent windings can be stacked against and bonded to each other or laterally spaced, and an inner surface of the series of windings, when inflated, can define the passage. The elongate shaft can be eccentrically attached to a distal portion of the balloon and its lumen can be in fluid communication with the interior of the inflatable tube. The inflatable tube can include two different polymer tubes, one slightly smaller than the other. The smaller, inner tube can be formed from a polymer having sufficient radial stiffness to resist collapse or bursting when exposed to inflation pressures, and the larger, outer tube can be formed from a polymer configured to exhibit adhesive properties when heated.

The present methods for sealing a perforation or dissection or dilating occlusive material can include inserting a guidewire into a blood vessel and advancing the guidewire to or across a treatment site, passing a perfusion catheter over the guidewire until a distal portion of the perfusion catheter is positioned near or within the treatment site, and inflating a balloon of the perfusion catheter. Inflating the balloon can include inflating a series of windings of helically-wound tubing, which may be contacting or laterally spaced. The balloon, upon inflation, can move from a deflated configuration to an inflation configuration at which an outer surface of the balloon can engage a wall of the blood vessel and an inner surface of the balloon can define a passage. The passage can allow a flow of bodily fluid, such as blood, through the perfusion catheter. Optionally, the method can include passing a treatment device at least partially through the passage. After treatment, the balloon can be deflated in a distal-to-proximal direction and removed through the guide catheter.

Objects of the present perfusion catheters and related methods include, among others:

1. Sealing a vessel perforation or dissection by blocking the injury from inside the vessel for an extended period of time while maintaining a sufficient flow of blood through a treated vessel segment;

2. Dilating a vessel occlusion for an extended period of time while maintaining a sufficient flow of blood through a treated vessel segment;

3. Delivering or receiving one or more treatment devices while sealing a vessel perforation or dissection or dilating a vessel occlusion; and/or 4. Cleanly removing all treatment devices.

These and other examples and objects of the present perfusion catheters and related methods will be set forth in the following Detailed Description. This Overview is intended to provide non-limiting examples of the present subject matter—it is not intended to provide an exclusive or exhaustive explanation. The Detailed Description below is included to provide further information about the present perfusion catheters and related methods.

BRIEF DESCRIPTION OF THE DRAWINGS

In the drawings, like numerals can be used to describe similar features and components throughout the several views. The drawings illustrate generally, by way of example but not by way of limitation, various embodiments discussed in the present patent document.

FIG. 15 illustrates a method of using a present catheter to navigate through vasculature, as constructed in accordance with at least one embodiment.

Figure 1:
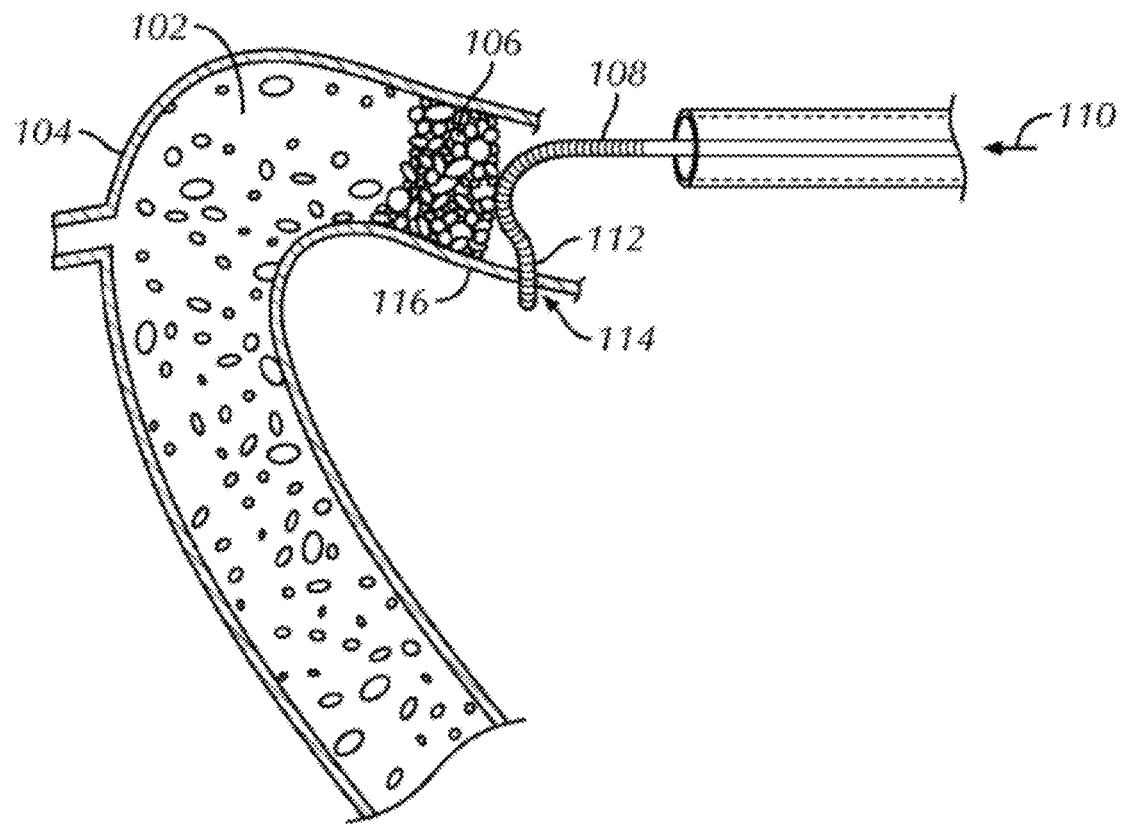
FIG. 1 illustrates a schematic view of a guidewire advanced through a patient's vasculature and unable to penetrate an end cap of an occlusion within a vessel.

The drawing figures are not necessarily to scale. Certain features and components may be shown exaggerated in scale or in schematic form and some details may not be shown in the interest of clarity and conciseness.

DETAILED DESCRIPTION

With the advancement of medical devices and increased training, clinicians are treating CTOs using angioplasty techniques more than ever before. The present catheters and methods provide the clinicians with a means to treat complications related to CTO angioplasty interventions or to dilate a vessel occlusion while maintaining a passage through the treated vessel segment. The present catheters and methods also provide the clinicians with a means to safely and effectively remove all interventional devices after treating a CTO. While the catheters and methods are primarily discussed in relation to treatment of coronary arteries, they may also be useful in other blood vessels throughout the body including peripheral arteries and veins.

Figure 2:
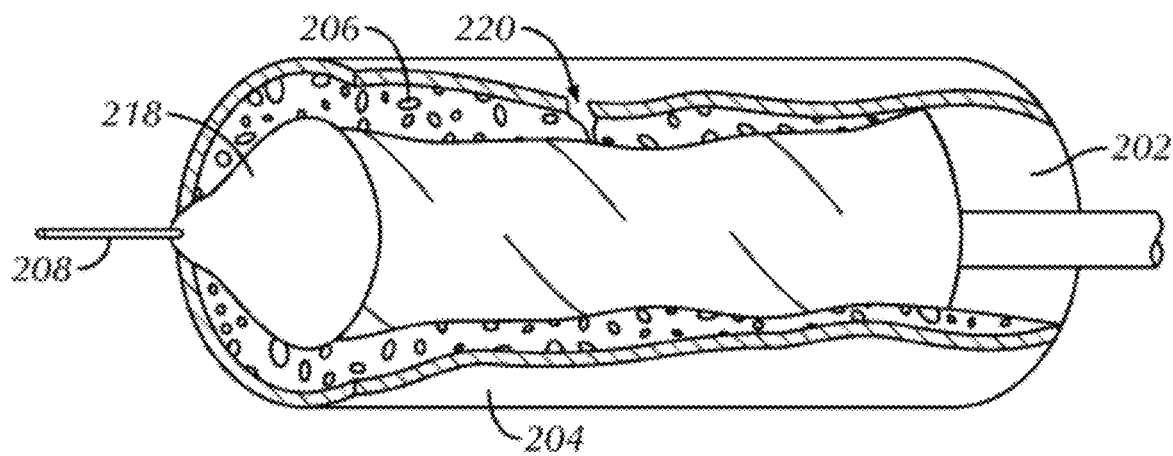
FIG. 2 illustrates a schematic view of a distal portion of a treatment device dilating an occlusion within a vessel segment, such dilation causing dissection of the vessel's wall.

FIGS. 1 and 2 provide examples of complications related to CTO angioplasty interventions in which the present perfusion catheters and related methods can be beneficial. In patients suffering from a CTO, successful treatment of the occlusion can be challenging. A factor that can determine whether a treating clinician can successfully treat the occlusion is the clinician's ability to advance a guidewire from a first side of the occlusion to a second side of the occlusion. In some instances, such as when the natural lumen 102 of a blood vessel 104 is totally occluded by hard plaque 106 (e.g., calcified atherosclerotic plaque), the guidewire 108 cannot cross the occlusion and, in response to a continued proximally-applied pushing force 110, its distal portion 112 may deviate to, and perforate 114, an adjacent vessel wall 116, as shown in FIG. 1.

In other instances, such as when the occlusive material 206 is soft or where the occlusion has a tiny opening, the guidewire 208 can be forced through the occlusive material and allowed to remain within the natural lumen 202 of the blood vessel 204. A treatment device, such as a balloon catheter 218, can be guided over the guidewire 208 to the occlusion site where it can be used to carry out dilation treatment. Mechanical dilatation of the vessel 204 with the balloon catheter 218 can be associated with plaque fracture, intimal wall splitting, and localized medial dissection. Dissection 220, if it occurs, may propagate into the media and through the adventitia (the outermost layer of the vessel wall), resulting in another form of coronary perforation as shown in FIG. 2.

Perforations and dissections are serious complications for a catheterization laboratory because of their associated morbidity and mortality rates and, for this reason alone, their management and treatment is important and should be initiated quickly. A first step in management and treatment can be the placement of a balloon to seal the perforation or dissection. Prolonged balloon inflation may successfully seal the perforation or stop the propagation of the dissection and can provide time to prepare and implant a covered stent, if needed.

The present perfusion catheter 300 can be used in cases where there is a vessel perforation or dissection to be treated and further in cases where there is occlusive material to be dilated. The catheter 300 can be advanced through a guide catheter and directed through vasculature for treatment of the vessel wall injury using a guidewire and optionally a placement catheter. The perfusion catheter 300 can include a proximal manifold 324 for coupling with an inflation syringe, an elongate shaft 326, and a distal balloon 328 to seal the perforation or dissection or dilate the occlusive material.

The elongate shaft 326 can serve two primary purposes. First, the elongate shaft 326 can transmit forces applied by a clinician to either advance or retract the perfusion catheter 300, and specifically the balloon 328, during an angioplasty or sealing procedure. By manipulating the elongate shaft 326, the balloon 328 can be inserted into and passed through a guide catheter and out the distal portion of the guide catheter to a perforation or dissection to be sealed or an occlusion to be dilated. Second, the elongate shaft 326 includes a lumen 330 for providing inflation fluid to, or withdrawing inflation fluid from, the balloon 328. The lumen 330 of the elongate shaft 326 can be in fluid communication with the manifold 324, couplable to an inflation syringe, at its proximal portion 332, and it can be in fluid communication with the interior of the balloon 328 near its distal portion 334.

The elongate shaft 326 can be eccentrically attached to a distal portion 336 of the balloon 328 and can extend proximally for clinician accessibility outside the guide catheter. The elongate shaft 326 can be attached to the balloon 328 by wrapping the balloon 328 about the shaft's intermediate 338 or distal 334 portions and affixing it thereto. In an example, the elongate shaft 326 is attached to the distal portion 336 of the balloon 328 for a minimum of 5 mm.

Figure 3:
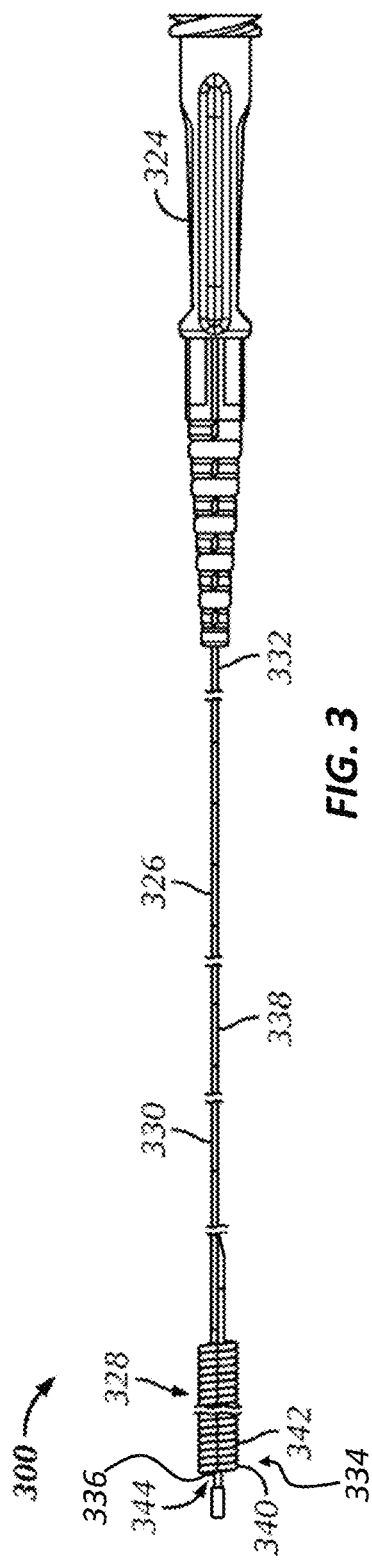
FIG. 3 illustrates a side view of a perfusion catheter, as constructed in accordance with at least one embodiment.

The embodiment of FIG. 3 illustrates that the balloon 328 can be formed from an inflatable tube 340 coiled in a helical or spiral manner around a central axis into a series of windings 342 (or loops), with consecutive or adjacent windings 342. The windings 342 may be stacked against and contacting each other with substantially no space therebetween, which can ensure the windings 342 act as a unit. Alternatively, the windings 342 may be spaced apart such that adjacent windings do not contact each other. Spaced windings 342 may be preferred for non-coronary applications, which may involve positioning the balloon 328 in veins of greater diameter. The inner surfaces of the windings 342 can define a passage 344 through the open center of the helix when the coiled balloon 328 is inflated. The passage 344 can extend the full length of the balloon 328 to permit blood or other fluid to perfuse (or flow) therethrough, which is important since cutting off blood supply for extended periods of time is undesirable. When the balloon 328 is deflated, it can collapse or flatten into a low profile configuration, which may comprise one or more folds that wrap around the distal portion 334 of the elongate shaft 326. An elastic sheath can optionally be disposed around the balloon 328 and be utilized to reduce the collapsed profile of the deflated balloon so that it can be more easily inserted or removed from a patient.

Because the passage 344 is created by the balloon 328, blood flow is permitted through the passage 344 and the overall perfusion catheter 300 can be kept to a minimal size. This physical attribute allows the catheter 300 to be of a small diameter when it is inserted into the patient's body and maneuvered to the desired position, yet provides a relatively large blood flow passage when the balloon 328 is inflated.

Figure 4:
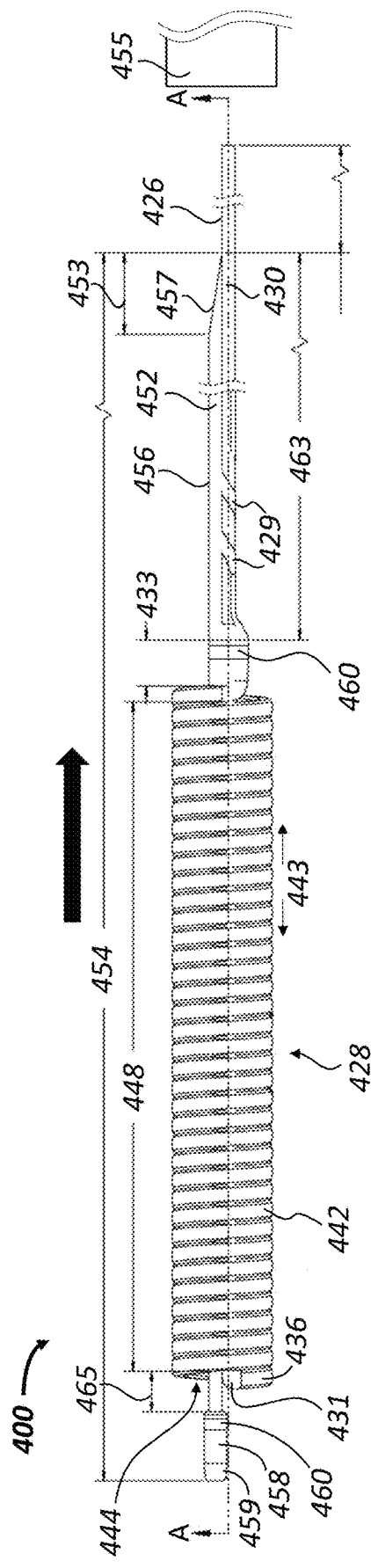
FIG. 4 illustrates an enlarged side view of a distal portion of a perfusion catheter including a dedicated guidewire lumen, as constructed in accordance with at least one embodiment.

FIG. 4 illustrates an enlarged side view of a distal portion of a perfusion catheter 400, as constructed in accordance with at least one embodiment. The catheter 400 can be provided with a guidewire lumen 452 separate from a passage 444 defined by windings 442 of a balloon 428 and separate from a lumen 430 of an elongate shaft 426 for providing inflation fluid to, or withdrawing inflation fluid from, the balloon 428. In the example shown, the windings 442 are stacked against each other, but in additional embodiments, the windings can be spread apart, such that a lateral space 443 is defined between them. The guidewire lumen 452 can have a length 454 approximately equal to, or slightly longer than, the length 448 of the passage 444 and can be positioned therein. An outer surface of a guidewire support tube 456 forming the guidewire lumen 452 can contact inner surfaces of the windings 442 of the balloon 428 and can optionally be inset in these inner surfaces. Polymers of the guidewire support tube 456 and the balloon 428 can be configured to adhere to each other upon application of heat treatment. A proximal end 457 of the guidewire support tube 456 may defined a skived entry configured to receive the guidewire in some examples. In various examples, the proximal end 457 may define a length 453 ranging between 2 mm and 5 mm, inclusive. In some embodiments, the elongate shaft 426 and the proximal end 429 of the balloon 428 may be fused together along a distance 463 of the guidewire lumen 452.

A distal end 436 of the balloon 428 is fluidly coupled with a distal end 431 of the lumen 430 of the elongate shaft 426, such that inflation fluid is added and removed at the distal end 436 of the balloon. The balloon 428 can be helically coiled proximally from its distal end 436, and a proximal end 429 of the balloon 428 may comprise a tail portion wrapped around the inflation lumen 430, thereby sealing the proximal end 429. Proximal wrapping of the balloon 428 may be implemented without heat shrinking or adhesive application in various implementations. Because the proximal end 429 of the balloon 428 can be sealed and inflation fluid can only be removed via its distal end 436, deflation of the balloon 428 may occur in a distal-to-proximal direction, in the direction of the arrow toward a guide catheter 455. Accordingly, when the catheter 400 is deflated and pulled proximally back into a guide catheter, the inflation fluid may not become trapped or sequestered in any portion of the balloon 428. This facilitates effective and safe removal of the catheter 400 from a treatment site, for example by decreasing the cross-sectional diameter of the deflated balloon. Complete deflation may also reduce the risk of puncturing or tearing the balloon 428 upon its reentry into the guide catheter 455. In examples, a maximum distance 433 of about 2 mm of the balloon may not be reflowed.

The guidewire lumen 452 can be designed to receive and facilitate tracking of a previously positioned guidewire having its distal portion in position near or across a treatment site. The perfusion catheter 400, and specifically the guidewire support tube 456, can be slid over the guidewire and advanced to the treatment site. An inner diameter of the guidewire support tube 456 can be sized to be advanced over a 0.36 mm (0.014 in) guidewire, for example. An atraumatic distal end portion 458 culminating in a tapered tip 459 can be disposed at a distal tip of the guidewire support tube 456 to prevent the perfusion catheter 400 from perforating a blood vessel during deployment and use. In various examples, a proximal portion of the distal end portion 458 can be distally offset by a distance 465 ranging from about 0.1 mm-5 mm. Since the guidewire support tube 456 can be short compared to the total lengths of the catheter 400 and the guidewire, the use of the guidewire support tube 456 as a guide permits rapid exchange of the catheter 400 over the guidewire.

One or more radiopaque markers 460 can be placed on the guidewire support tube 456 or the elongate shaft 426 proximal or distal to the balloon 428. These markers 460 can facilitate proper placement of the balloon 428 relative to a vessel wall injury prior to its inflation and can be any suitable radiopaque material detectable through the use of x-ray or fluoroscopy. Materials such as the platinum series of metals (e.g., platinum or palladium), gold, silver, iridium, or tantalum can be used as the markers. Certain stainless steels can also be suitable for use as markers. Alternatively, the polymer used in portions of the perfusion catheter 400 can be radiopaque or made so by addition of filler such as barium sulfate, bismuth trioxide, bismuth carbonate, tungsten, tantalum, or the like.

Figure 5:
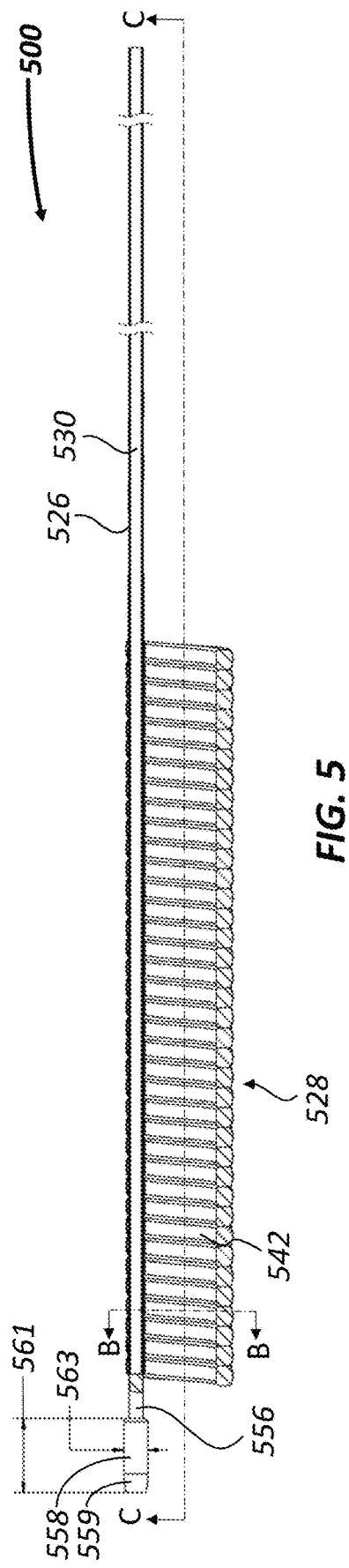
FIG. 5 illustrates an enlarged cross-sectional view of a distal portion of the perfusion catheter taken along line A-A of FIG. 4.

FIG. 5 illustrates a cross-sectional view of a catheter 500 (taken along line A-A of FIG. 4). As shown, the inflation lumen 530 of the elongate shaft 526 can longitudinally span the length of the balloon 528, such that each of the plurality of windings 542 covers the elongate shaft 526. The guidewire support tube 556 can extend for a distance beyond the distal end of the elongate shaft. In the embodiment shown, the distal end portion 558 of the guidewire support tube 556, including the tapered tip 559, can define a length 561 of about 3 mm. The length 561 may vary in examples, ranging from about 1 mm to about 6 mm, about 2 mm to about 5 mm, or about 1.5 mm to about 4.5 mm. The diameter or width 563 of the distal end portion 558 may also vary. In various embodiments, the maximum width of the distal end portion may be about 0.038 in. The minimum width may be adjustable, provided the width is sufficient to accommodate a guidewire for various applications. In examples, the width 563 may range from about 0.01 in to about 0.05 in.

Figure 6:
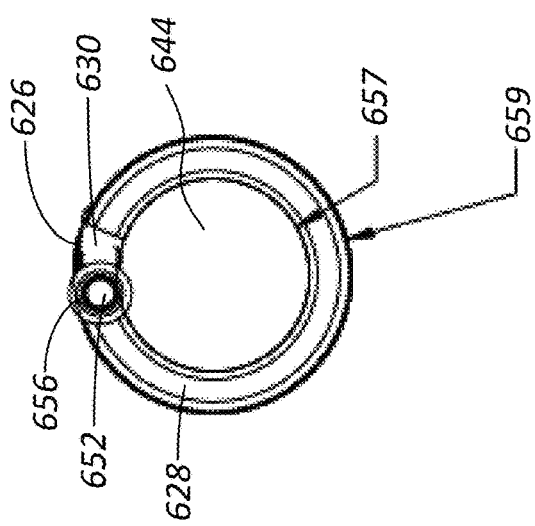
FIG. 6 illustrates an enlarged cross-sectional view taken along line B-B of FIG. 5.

FIG. 6 illustrates a cross-sectional view of an inflated balloon 628 and a guidewire support tube 656 and elongate shaft 626 extending therethrough, taken along line B-B of FIG. 5. The guidewire support tube 656 and the elongate shaft 626 can be inset or embedded within a radial portion of the inflatable tube comprising the balloon 628, leaving the internal passage 644 unobstructed upon inflation of the balloon 628. In examples, the balloon windings can be bonded directly to the guidewire support tube 656 for the full length of the balloon, such that the guidewire lumen 652 and inflation lumen 630 are fully enveloped by the balloon. In some embodiments, an outer surface of the elongate shaft 626 and the distal end of the inflatable balloon 628 can be affixed by a heat treatment process such that the shaft's lumen is in fluid communication with an interior of the balloon.

The inner diameter 657 of the inflated balloon 628 can accommodate passage of various treatment devices, e.g., stents, therethrough. The inner diameter 657 may be about 3 mm in some examples, and can range in additional implementations from about 1 mm to about 6 mm, about 2 mm to about 5 mm, or about 1.5 mm to about 4.5 mm. The outer diameter 659 can also vary, depending for example on the diameter of a vessel at the targeted treatment site. In various embodiments, the outer diameter 659 can range from about 2 mm to about 8 mm, about 3 mm to about 6 mm, about 3.5 mm to about 5 mm, about 3.75 mm to about 4.25 mm, or about 4 mm.

Figure 7A:
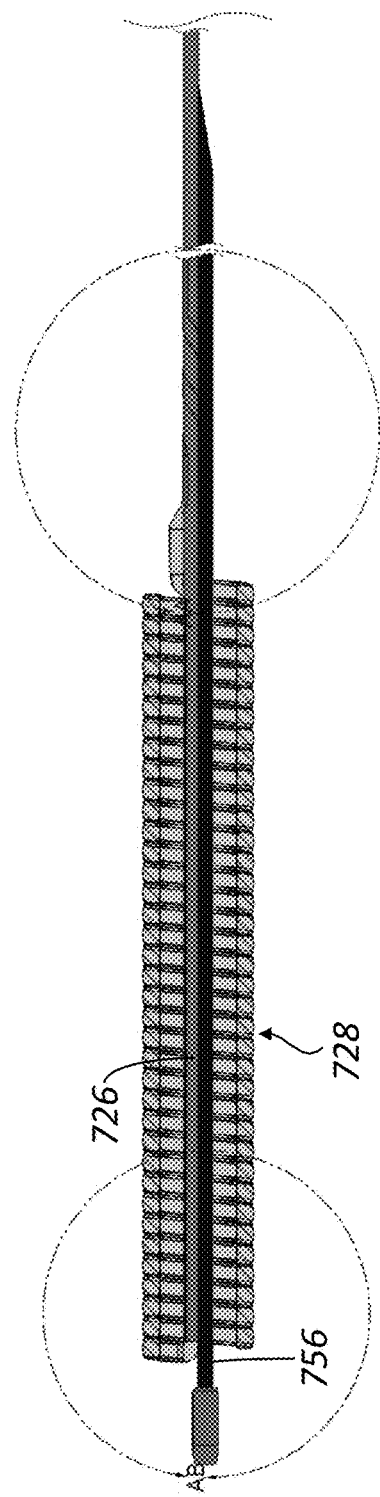
FIG. 7A illustrates an enlarged cross-sectional view taken along line C-C of FIG. 5.
Figure 7C:
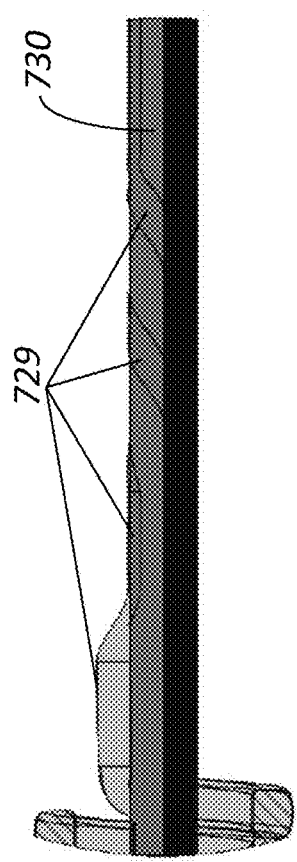
FIG. 7C illustrates an enlarged cross-sectional view taken at detail AA of FIG. 7A.
Figure 7B:
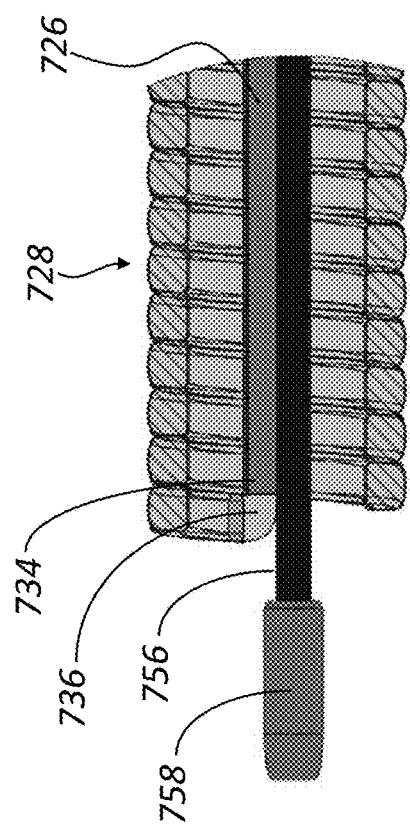
FIG. 7B illustrates an enlarged cross-sectional view taken at detail AB of FIG. 7A.

FIG. 7A illustrates a cross-sectional view of a catheter 700, taken along line C-C of FIG. 5. As shown, the elongate shaft 726 and guidewire support tube 756 can be positioned adjacent to each other, each embedded within the balloon 728. FIG. 7B provides an enlarged view of detail AB, showing where the fluid connection between a distal portion 734 of the elongate shaft 726 and a distal portion 736 of the balloon 728 can be established, proximal to the distal end portion 758 of the guidewire support tube 756. FIG. 7C provides an enlarged view of detail AA, showing the proximal end 729 portion of the balloon, which in the example shown, comprises a tail portion wrapped around the inflation lumen 730.

Figure 8:
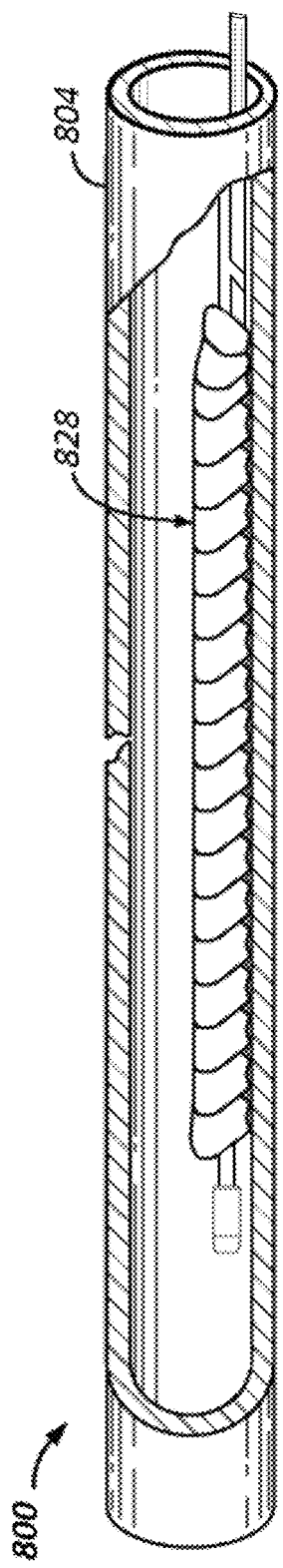
FIG. 8 illustrates an enlarged side view of a distal portion of the perfusion catheter shown in FIG. 4, with its balloon in a deflated configuration within a vessel segment.

FIG. 8 illustrates a perfusion catheter 800 in a blood vessel 804 of a patient. The catheter 800, and specifically a balloon 828 of the catheter, can be introduced and advanced within the blood vessel 804 in a low profile, unexpanded configuration. In this configuration, the balloon 828 is in a relaxed, folded, or crushed configuration and does not significantly increase the overall diameter of a distal portion of the catheter 800 such that it can be inserted into the patient and guided through the patient's vasculature to the desired treatment site.

Figure 9:
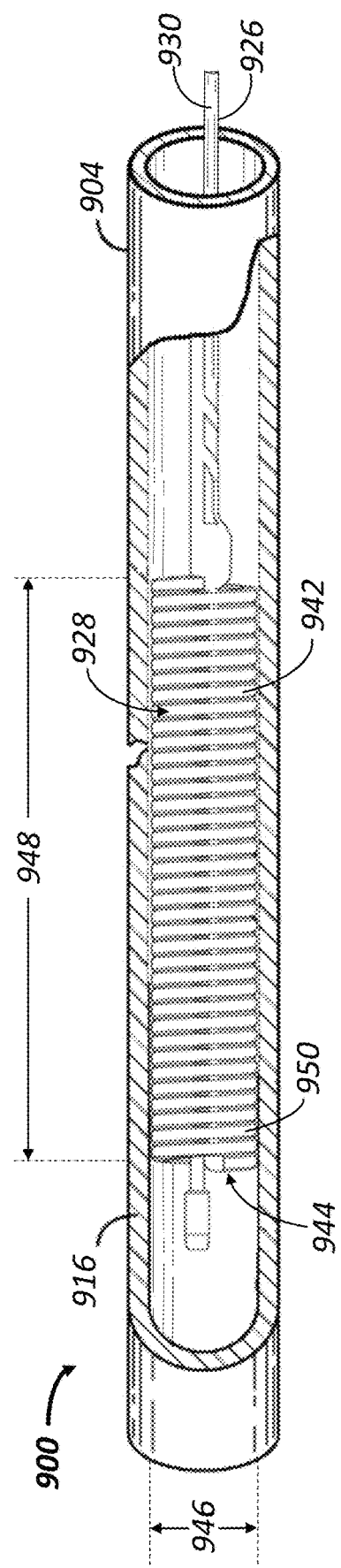
FIG. 9 illustrates an enlarged side view of a distal portion of the perfusion catheter shown in FIG. 4, with its balloon in an inflated configuration within a vessel segment.

Once at the treatment site, the balloon 928 can be inflated as illustrated in FIG. 9. Fluid under pressure can be supplied to the balloon 928 through an inflation lumen 930 of an elongate shaft 926, thereby expanding the balloon 928 toward a wall 916 of the blood vessel 904, such as for sealing, opening, or otherwise treating it. When inflated, the balloon 928 can impinge upon or engage the vessel wall 916 at the treatment site at pressures of 2 atm-20 atm, for example, yet blood can be allowed to flow through the passage 944 defined by the balloon's windings 942. Since the passage 944 created through the windings 942 is relatively large compared to the size of the vessel 904, the interruption of blood flow through the vessel is minimized and the perfusion catheter 900 is capable of prolonged inflation for temporary hemostasis in coronary perforations or dissections.

Beyond allowing for fluid flow, the passage 944 of the balloon 928 can be adapted to slidably receive a treatment device (e.g., a smaller diameter balloon catheter, stent catheter, guidewire support catheter, or guidewire). The balloon 928 can include any number of windings 942 in a number of sizes and configurations depending upon the particular treatment site, procedure and/or patient. Increasing the number of windings 942 in the balloon 928 can increase the ability of the balloon 928 to maintain a dilated state of an occlusion. The passage 944 can have a diameter 946 ranging from 2 mm-6 mm and can extend 10 mm-50 mm in length 948, for example. The diameter 946 of the passage 944 can be sufficiently large to permit entry of a stent catheter. The present inventors recognize that plaque has a tendency to return to its original form and restrict passage. This restenosis, if it occurs, can occur as quickly as a few minutes. The perfusion catheter 900 allows the stent catheter to be delivered through the catheter while the balloon 928 dilates the occlusion. In this way, there can be minimal time between occlusion dilation and placement of a stent. The diameter 946 of the passage 944 can be sufficiently large to receive a guidewire support catheter to help pre-dilate or otherwise establish a pilot opening through the occlusion, or to receive the distal portion of a retrograde guidewire that is funneled into the passage 944 as a result of engagement between an outer surface 950 of the balloon 928 and the vessel wall 916.

When the procedure is completed, the balloon 928 can be deflated by applying vacuum to a proximal manifold coupled with the inflation lumen 930 of the elongate shaft 926. The entire perfusion catheter 900 can then be removed.

Figure 10:
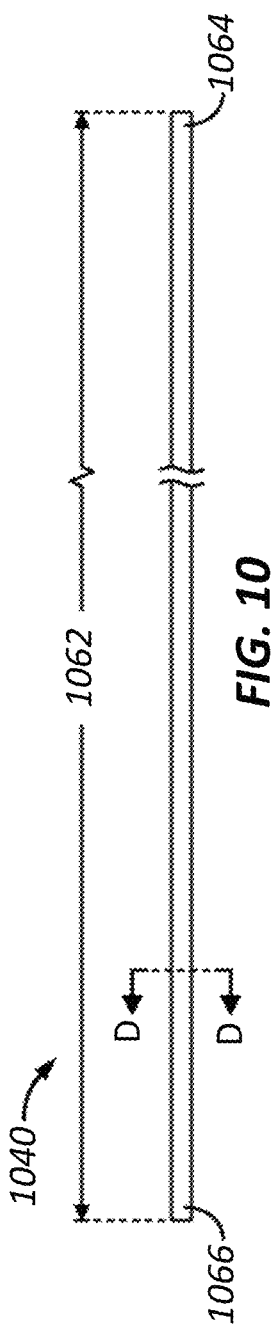
FIG. 10 illustrates an enlarged side view of a distal view of a distal portion of a perfusion catheter including a dedicated guidewire lumen, as constructed in accordance with at least one embodiment.
Figure 11:
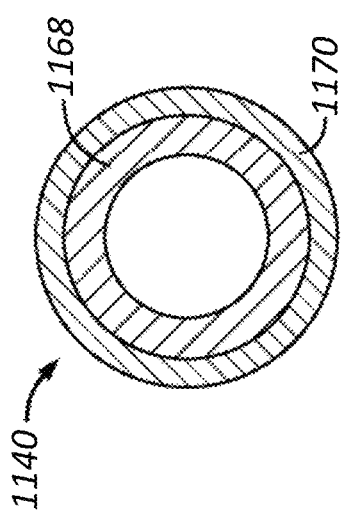
FIG. 11 illustrates a cross-sectional view taken along line D-D of the extruded tubing shown in FIG. 10.

FIGS. 10 and 11 respectively illustrate side and cross-sectional views of extruded tubing 1040 for use in a balloon of a perfusion catheter, as constructed in accordance with at least one embodiment. The extruded tubing 1040 can have a uniform outer diameter along its length 1062 or can have a larger diameter along a majority of its length and tapered down on its proximal 1064 and distal 1066 portions. The length 1062 of the extruded tubing 1040 can range from 40 cm-120 cm before being coiled in a helical or spiral manner into a series of windings.

The coiled shape of the balloon can be maintained by causing adjacent windings to adhere to one another, in some examples, and the integrity of the balloon can be internally provided within each winding. These qualities can be accomplished by coextruding a combination of nested polymers which, after winding of the coil, can be heat treated to allow adjacent coils to stick to each other. In the example of FIG. 11, the extruded tubing 1140 is formed by coextruding two different polymer tubes 1168, 1170 (or layers), one slightly smaller than the other. The coextrusion process can eliminate seams, which are found in existing balloon designs, form tight bonds, and create a balloon using a reduced number of manufacturing steps. Alternatively, the smaller tube 1168 can be inserted inside the larger tube 1170 post-extrusion.

The smaller, inner tube 1168 can be formed from a polymer having sufficient radial stiffness to resist collapse or bursting when exposed to inflation pressures, and the larger, outer tube 1170 can be formed from a polymer configured to exhibit adhesive properties when heated and compliant properties when used within the body. In some examples, the adhesive properties of the outer tube 1170 can allow adjacent windings to adhere to one another. The use of a compliant material for the outer tube 1170 can enable the balloon to conform to a vessel wall at the site of a perforation or tear, so that a substantial portion of the balloon's outer surface can be compressed against the vessel wall, or at the site of an occlusion that can benefit from being dilated. In various examples, the inner tube 1168 can include polyethylene terephthalate (PET) or PEBAX polyether block amides (which are available from Arkema) having an outer diameter of 0.2 mm-0.28 mm and an inner diameter of 0.12 mm-0.18 mm, and the outer tube 1170 can include HYTREL polyester elastomer (which is available from E.I. du Pont de Nemours and Company), PEBAX, or nylon having an outer diameter of 0.28 mm-0.36 mm and an inner diameter of 0.20 mm-0.28 mm. The inner 1168 and outer 1170 tubes can include polymers having different melting or softening temperatures, with the inner tube 1168 including the polymer with the higher melting temperature. The inner 1168 and outer 1170 tubes can include the same or similar polymers, with the polymer of the inner tube 1168 being cross-linked for strength and with the polymer of the outer tube 1170 not being cross-linked.

Figure 12:
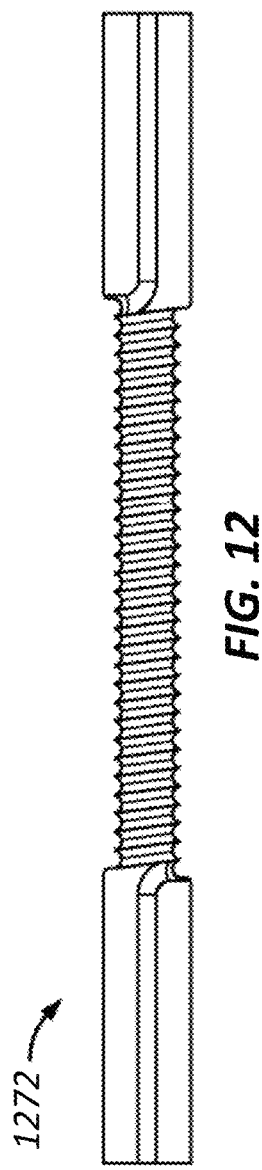
FIG. 12 illustrates a mandrel for manufacturing a balloon of a perfusion catheter, as constructed in accordance with at least one embodiment.

FIG. 12 illustrates a mandrel 1272 for coiling extruded tubing in a helical manner around a central axis into a series of windings to form a balloon. The extruded tubing can be wrapped in a proximal direction about the mandrel 1272, which includes a shape of the intended profile of the balloon. After being wrapped onto the mandrel 1272, the extruded tubing can be pressurized or inflated and adjacent windings can be heat set in order to ensure that they adhere to one another and the balloon maintains its coiled shape. For example, heat setting the coiled configuration of the balloon can include causing the outer surface of adjacent windings of the extruded tubing to adhere to one another via heating the tubing or the mandrel 1272. The extruding tubing can then be cooled to room temperature. In additional examples, adjacent windings may not be heat set in order to ensure that the windings remain laterally spaced from each other upon inflation.

Figure 13:
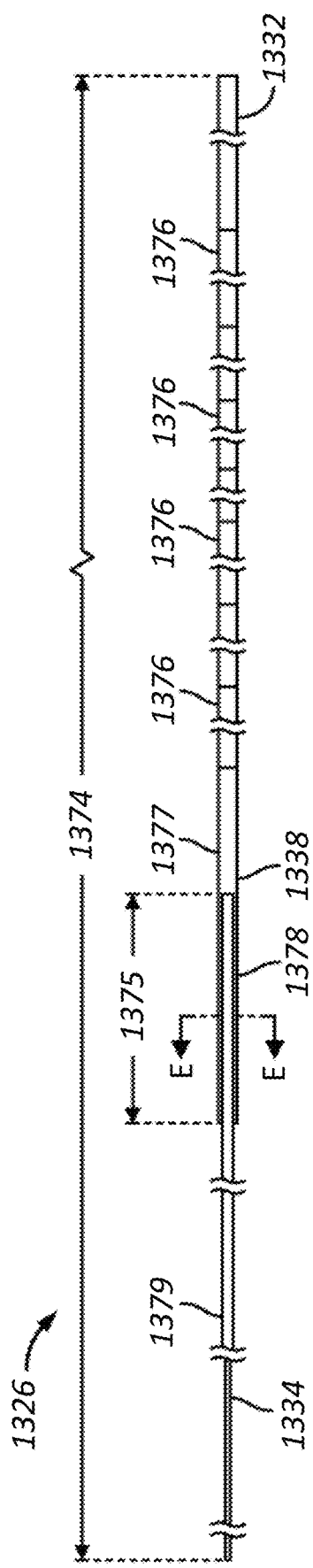
FIG. 13 illustrates a side view of an elongate shaft of a perfusion catheter, as constructed in accordance with at least one embodiment.
Figure 14:
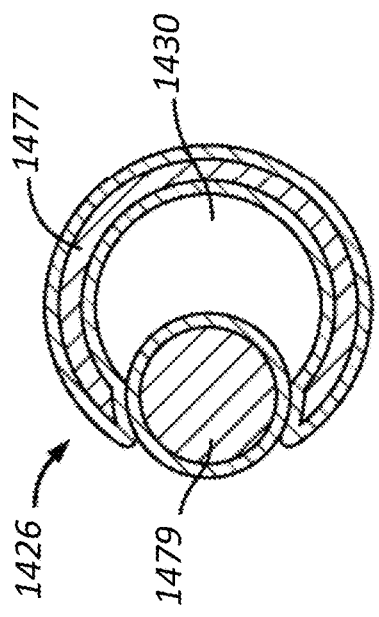
FIG. 14 illustrates a cross-sectional view taken along line E-E of the elongate shaft shown in FIG. 13.

FIGS. 13 and 14 respectively illustrate side and cross-sectional views of an elongate shaft 1326, 1426 of a perfusion catheter, as constructed in accordance with at least one embodiment. The elongate shaft 1326, 1426 can include a lumen 1430 extending from a proximal portion 1332 to an inflation port for providing inflation fluid to, or withdrawing inflation fluid from, a distal end of a distal balloon. The elongate shaft 1326, 1426 can extend a length 1374 of 100 cm-200 cm and can possess the qualities of compression rigidity along its longitudinal axis, which facilitates advancement of the perfusion catheter through a patient's vascular system, and good distal flexibility, which enhances maneuverability of catheter through directional changes of the vascular system and prevents damage to the vessel walls as it is being inserted. Portions of the elongate shaft 1326, 1426 can include a PTFE coating 1376 to facilitate its advancement through the patient's vascular system.

These qualities are achievable in a variety of ways. In an example, proximal 1332 and intermediate 1338 portions of the elongate shaft 1326, 1426 can include a stainless steel hypotube 1377, 1477, and the distal portion 1334 can include a stainless steel support wire 1379, 1479 or tube that is connected for a length 1375 to the intermediate portion. The support wire 1379, 1479 can help transmit forces applied by a treating clinician to either advance or retract the balloon during a treatment procedure. The support wire 1379, 1479 can range in length from 10 cm-20 cm and can be secured to the hypotube 1377, 1477 via a laser weld. The support wire 1379, 1479 can extend to a location distal to the balloon or can terminate between the balloon's proximal and distal portions. In another embodiment, the elongate shaft 1326, 1426 can be formed from a single piece of metallic or polymer tubing with a proximal portion that has an outer and inner diameter larger than an outer and inner diameter of a distal portion or with a proximal portion having greater wall thickness than a distal portion.

A means to affix an outer surface 1378 of the elongate shaft 1326, 1426 and the flexible material of the balloon can be employed to withstand stresses associated with pressure changes of inflation and deflation of the balloon. It can be important that the affixing means create a fluid tight seal between the two materials and restrict any delamination along the seal line during prolong periods of working pressures. In an example, portions of the elongate shaft 1326, 1426 coupled with the balloon can be covered with nylon (e.g., VESTAMID L2101) as part of the affixing means. The materials can be joined by an adhesive process, such as a cyanoacrylate, epoxy or urethane compounds, or joined by a heat treatment or pressure fit process that melts or welds the two materials together.

FIG. 15 illustrates a method 1500 of using a perfusion catheter in a coronary vessel for sealing a perforation or dissection or dilating occlusive material while maintaining a passage.

At 1582, the method involves passing a perfusion catheter, including a balloon and an elongate shaft that is attached to the balloon, into a blood vessel until the balloon is positioned adjacent a perforation or dissection in a wall of the blood vessel.

At 1584, the method involves inflating the balloon to seal the perforation or dissection in the wall of the blood vessel. Inflation of the balloon can include urging fluid through a lumen of the elongate shaft and into the balloon to inflate a series of helical windings.

At 1586, the method specifies that the balloon, upon inflation, moves from a deflated configuration to an inflated configuration at which an outer surface of the balloon engages the wall of the blood vessel and an inner surface of the balloon's series of helical windings defines a passage.

At 1588, the method involves, after inflating the balloon, passing a treatment device at least partially through the passage. The treatment device can be received in a distal-to-proximal direction or delivered in a proximal-to-distal direction.

At 1590, the method involves deflating the balloon by withdrawing fluid from the balloon in a distal-to-proximal direction of the balloon.

At 1592, the method involves retracting the perfusion catheter from the blood vessel. Additional or alternative steps may be incorporated into method 1500 in accordance with the present disclosure.

CLOSING NOTES

The above Detailed Description includes references to the accompanying drawings, which form a part of the Detailed Description. The Detailed Description should be read with reference to the drawings. The drawings show, by way of illustration, specific embodiments in which the present catheters and related methods can be practiced. These embodiments are also referred to herein as "examples."

The Detailed Description is intended to be illustrative and not restrictive. For example, the above-described examples (or one or more features or components thereof) can be used in combination with each other. Other embodiments can be used, such as by one of ordinary skill in the art upon reviewing the above Detailed Description. Also, various features or components have been or can be grouped together to streamline the disclosure. This should not be interpreted as intending that an unclaimed disclosed feature is essential to any claim. Rather, inventive subject matter can lie in less than all features of a particular disclosed embodiment. Thus, the following claim examples are hereby incorporated into the Detailed Description, with each example standing on its own as a separate embodiment:

In a first example, a perfusion catheter can include an inflatable balloon coiled in a helical manner around a central axis into a series of windings. An inner surface of the series of windings, when inflated, can define a passage through the inflatable balloon. The catheter can also include an elongate shaft extending from a proximal portion to a distal portion, having an inner surface that defines a lumen for providing inflation fluid to, or withdrawing inflation fluid from, a distal end of the inflatable balloon. The catheter can further include a guidewire support tube including a lumen, separate from the lumen from the elongate shaft and the passage through the inflatable balloon, for receiving a guidewire.

In some examples, the perfusion catheter can optionally be configured such that the guidewire support tube is inset in the inner surface of the series of windings. In some examples, the perfusion catheter can optionally be configured such that an outer surface of the elongate shaft and the distal end of the inflatable balloon are affixed by a heat treatment process such that the shaft's lumen is in fluid communication with an interior of the balloon. In some examples, the passage can have a diameter ranging from 2 mm-6 mm and a length ranging from 10 mm-50 mm. In some embodiments, the elongate shaft can be eccentrically positioned relative to the inflatable balloon such that the elongate shaft does not protrude radially into the passage. In some examples, a proximal portion of the inflatable balloon can wrap around the elongate shaft, such that the proximal portion is sealed. In some examples, the guidewire support tube and the elongate shaft can be inset in the inner surface of the series of windings. In some examples, the inflatable balloon can be configured to deflate in a distal-to-proximal direction. In some examples, the inflatable balloon can include concentric inner and outer tubes, a polymer of the inner tube can be cross-linked, a polymer of the outer tube can be non-cross-linked, and the polymer of the inner tube can have sufficient radial stiffness to resist bursting when exposed to inflation pressure. In some examples, adjacent windings of the series of windings can be stacked against and bonded to each other through adhesive properties of the polymer of the outer tube when heated. In some examples, a distal portion of the guidewire support tube can protrude distally beyond the distal end of the inflatable balloon by 2 mm-8 mm.

In accordance with some examples, a method can involve passing a perfusion catheter, including a balloon, and an elongate shaft that is attached to the balloon, into a blood vessel until the balloon is positioned adjacent a perforation or dissection in a wall of the blood vessel. The method can also involve inflating the balloon to seal the perforation or dissection in the wall of the blood vessel including urging fluid through a lumen of the elongate shaft and into the balloon to inflate a series of helical windings of the balloon. The balloon, upon inflation, can move from a deflated configuration to an inflated configuration at which an outer surface of the balloon engages the wall of the blood vessel and an inner surface of the balloon's series of helical windings defines a passage. After inflating the balloon, the method can involve passing a treatment device at least partially through the passage, including receiving, in a distal-to-proximal direction, or delivering, in a proximal-to-distal direction, a treatment device. The method can also involve deflating the balloon by withdrawing fluid from the balloon in a distal-to-proximal direction of the balloon, and retracting the perfusion catheter from the blood vessel.

In some examples, passing the perfusion catheter into the blood vessel can include advancing a guidewire through a guidewire support tube, which is separate from the lumen of the elongate shaft and the passage defined by the balloon's series of helical windings. In some examples, passing the perfusion catheter into the blood vessel can include advancing a guidewire through a guidewire support tube, which is inset into the inner surface of the balloon's series of helical windings. In some examples, inflating the balloon can include dilating occlusive material accumulation within the wall of the blood vessel. In some examples, inflating the balloon can involve urging the fluid into the balloon in a distal-to-proximal direction of the balloon. In some examples, deflating the balloon and retracting the perfusion catheter can occur simultaneously. In some examples, inflating the balloon can include inflating the balloon to a pressure between 2 atm-20 atm, inclusive. In some examples, delivering the treatment device to the treatment site or distal to the perforation or dissection can include guiding the treatment device along a path offset from an axis of the elongate shaft. In some examples, inflating the balloon can involve urging the fluid through a fluid connection at a distal end of the balloon and a distal end of the elongate shaft.

Certain terms are used throughout this patent document to refer to particular features or components. As one skilled in the art appreciates, different people may refer to the same feature or component by different names. This patent document does not intend to distinguish between components or features that differ in name but not in function.

For the following defined terms, certain definitions shall be applied unless a different definition is given elsewhere in this patent document. The terms "a," "an," and "the" are used to include one or more than one, independent of any other instances or usages of "at least one" or "one or more." The term "or" is used to refer to a nonexclusive or, such that "A or B" includes "A but not B," "B but not A," and "A and B." All numeric values are assumed to be modified by the term "about," whether or not explicitly indicated. The term "about" generally refers to a range of numbers that one of skill in the art would consider equivalent to the recited value (e.g., having the same function or result). In many instances, the term "about" can include numbers that are rounded to the nearest significant figure. The recitation of numerical ranges by endpoints includes all numbers and sub-ranges within and bounding that range (e.g., 1 to 4 includes 1, 1.5, 1.75, 2, 2.3, 2.6, 2.9, etc. and 1 to 1.5, 1 to 2, 1 to 3, 2 to 3.5, 2 to 4, 3 to 4, etc.). The terms "patient" and "subject" are intended to include mammals, such as for human or veterinary applications. The terms "distal" and "proximal" are used to refer to a position or direction relative to the treating clinician. "Distal" and "distally" refer to a position that is distant from, or in a direction away from, the treating clinician. "Proximal" and "proximally" refer to a position that is near, or in a direction toward, the treating clinician.

The scope of the invention should be determined with reference to the appended claims, along with the full scope of equivalents to which such claims are entitled. In the appended claims, the terms "including" and "in which" are used as the plain-English equivalents of the respective terms "comprising" and "wherein." Also, in the following claims, the terms "including" and "comprising" are open-ended; that is, a device, kit or method that includes features or components in addition to those listed after such a term in a claim are still deemed to fall within the scope of that claim. Moreover, in the following claims, the terms "first," "second" and "third," etc. are used merely as labels, and are not intended to impose numerical requirements on their objects.

The Abstract is provided to allow the reader to quickly ascertain the nature of the technical disclosure. It is submitted with the understanding that it will not be used to interpret or limit the scope or meaning of the claims.

What is claimed is:

1. A perfusion catheter, consisting of:
   an inflatable balloon coiled in a helical manner around a central axis into a series of windings, wherein an inner surface of the series of windings when inflated define a passage through the inflatable balloon;
   an elongate shaft extending from a proximal end to a distal end and having an inner surface that defines a lumen for providing inflation fluid to, and withdrawing inflation fluid from, the inflatable balloon, wherein the lumen of the elongate shaft is in fluid communication with an interior of the inflatable balloon solely at a distal end of the inflatable balloon such that inflation fluid is added and removed exclusively at the distal end of the inflatable balloon; and
   a guidewire support tube including a lumen for receiving a guidewire, the lumen of the guidewire support tube is separate from the lumen of the elongate shaft and the passage through the inflatable balloon.

2. The perfusion catheter of claim 1, wherein the elongate shaft includes an inflation port located at the distal end of the elongate shaft, the inflation port configured to provide inflation fluid to, and to withdraw inflation fluid from, the distal end of the inflatable balloon.

3. The perfusion catheter of claim 1, wherein a proximal end of the inflatable balloon is wrapped around the elongate shaft to seal the proximal end of the inflatable balloon.

4. The perfusion catheter of claim 1, wherein the inflatable balloon is configured to be deflated in a distal-to-proximal direction.

5. The perfusion catheter of claim 1, wherein the elongate shaft longitudinally spans a length of the inflatable balloon.

6. The perfusion catheter of claim 1, wherein the series of windings of the inflatable balloon surround the elongate shaft.

7. The perfusion catheter of claim 1, wherein the guidewire support tube is inset in the inner surface of the series of windings.

8. The perfusion catheter of claim 1, wherein the guidewire support tube and the elongate shaft are inset in the inner surface of the series of windings.

9. The perfusion catheter of claim 1, wherein a distal end of the guidewire support tube extends a distance beyond the distal end of the inflatable balloon.

10. The perfusion catheter of claim 9, wherein the distance is from 2 millimeters to 8 millimeters, inclusive.

11. The perfusion catheter of claim 1, wherein an outer surface of the elongate shaft and the distal end of the inflatable balloon are affixed by a heat treatment process such that the lumen of the elongate shaft is in fluid communication with the interior of the inflatable balloon.

12. The perfusion catheter of claim 1, wherein the passage has a diameter ranging from 2 millimeters to 6 millimeters, inclusive, and a length ranging from 10 millimeters to 50 millimeters, inclusive.

13. The perfusion catheter of claim 1, wherein the inflatable balloon includes concentric inner and outer tubes, a polymer of the inner tube is cross-lined, a polymer of the outer tube is non-cross-linked, and the polymer of the inner tube has sufficient radial stiffness to resist bursting when exposed to inflation pressure.

14. The perfusion catheter of claim 1, wherein adjacent windings of the series of windings are stacked against and bonded to each other through adhesive properties of a polymer of the inflatable balloon when heated.

15. The perfusion catheter of claim 1, wherein the inflatable balloon has a length in a range from 40 centimeters to 120 centimeters, inclusive, before being coiled into the series of windings.

16. The perfusion catheter of claim 1, wherein the series of windings of the inflatable balloon are configured to, when inflated, engage a vessel wall of a patient at a treatment site while allowing a flow of blood or movement of a treatment device through the passage.

17. The perfusion catheter of claim 1, wherein the inflatable balloon is configured to be deflated by applying a vacuum to a proximal manifold coupled with the proximal end of the elongate shaft.

18. A perfusion catheter, comprising:
    an inflatable balloon coiled in a helical manner around a central axis into a series of windings that are stacked against and bonded to each other, wherein an inner surface of the series of windings when inflated define a passage through the inflatable balloon;
    an elongate shaft extending from a proximal end to a distal end and having an inner surface that defines a lumen for providing inflation fluid to, and withdrawing inflation fluid from, the inflatable balloon, wherein the lumen of the elongate shaft includes an inflation port that is in fluid communication with an interior of the inflatable balloon in such a way that inflation fluid is exclusively added and removed from the distal end of the inflatable balloon; and
    a guidewire support tube including a lumen for receiving a guidewire, the lumen of the guidewire support tube separate from the lumen of the elongate shaft and the passage through the inflatable balloon, wherein the guidewire support tube is inset in the inner surface of the series of windings.

19. A perfusion catheter, comprising:
    an inflatable balloon coiled in a helical manner around a central axis into a series of spaced apart windings that do not contact each other, wherein an inner surface of the series of windings when inflated define a passage through the inflatable balloon;
    an elongate shaft extending from a proximal end to a distal end and having an inner surface that defines a lumen for providing inflation fluid to, and withdrawing inflation fluid from, the inflatable balloon, wherein the lumen of the elongate shaft includes an inflation port that is in fluid communication with an interior of the inflatable balloon in such a way that inflation fluid is exclusively added and removed from the distal end of the inflatable balloon; and a guidewire support tube including a lumen for receiving a guidewire, the lumen of the guidewire support tube separate from the lumen of the elongate shaft and the passage through the inflatable balloon, wherein the guidewire support tube is inset in the inner surface of the series of windings.

\* \* \* \* \*

UNITED STATES PATENT AND TRADEMARK OFFICE
CERTIFICATE OF CORRECTION

| | | |
|---|---|---|
| PATENT NO. | : 11,660,425 B2 | Page 1 of 1 |
| APPLICATION NO. | : 17/245725 | |
| DATED | : May 30, 2023 | |
| INVENTOR(S) | : Peterson et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 148 days.

Signed and Sealed this
Seventh Day of January, 2025

Derrick Brent
*Acting Director of the United States Patent and Trademark Office*